(12) United States Patent
Liu et al.

(10) Patent No.: US 8,569,322 B2
(45) Date of Patent: Oct. 29, 2013

(54) LAMIVUDINE OXALATE AND PREPARATION METHOD THEREOF

(75) Inventors: Yanlong Liu, Jiangsu (CN); Fei Liu, Jiangsu (CN); Xiquan Zhang, Jiangsu (CN)

(73) Assignee: Chia Tai Tianqing Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 13/581,268

(22) PCT Filed: Dec. 23, 2010

(86) PCT No.: PCT/CN2010/080151
§ 371 (c)(1),
(2), (4) Date: Nov. 5, 2012

(87) PCT Pub. No.: WO2011/103762
PCT Pub. Date: Sep. 1, 2011

(65) Prior Publication Data
US 2013/0053560 A1    Feb. 28, 2013

(30) Foreign Application Priority Data

Feb. 25, 2010   (CN) .......................... 2010 1 0132895

(51) Int. Cl.
*A61K 31/513*   (2006.01)
*C07D 239/22*   (2006.01)
*C07D 411/04*   (2006.01)

(52) U.S. Cl.
USPC ........... 514/274; 544/242; 544/298; 544/316; 514/256; 514/269

(58) Field of Classification Search
USPC .......... 544/242, 298, 315, 316; 514/256, 269, 514/274
See application file for complete search history.

(56) References Cited

U.S. PATENT DOCUMENTS

| | | | |
|---|---|---|---|
| 6,600,044 B2 * | 7/2003 | Murthy et al. ................. | 544/264 |
| 7,157,447 B2 * | 1/2007 | Naidu et al. ..................... | 514/80 |
| 7,192,948 B2 * | 3/2007 | Banville et al. ............ | 514/211.1 |
| 7,491,819 B1 * | 2/2009 | Naidu et al. .................. | 544/105 |

FOREIGN PATENT DOCUMENTS

| | | |
|---|---|---|
| CN | 101544632 A | 9/2009 |
| WO | 2008/053496 A2 | 5/2008 |

OTHER PUBLICATIONS

The International Search Report from PCT/CN2010/080151, dated Mar. 31, 2011.

* cited by examiner

*Primary Examiner* — Golam M M Shameem
(74) *Attorney, Agent, or Firm* — Kilpatrick Townsend & Stockton LLP

(57) ABSTRACT

Lamivudine oxalate, preparation method and crystalline forms thereof are disclosed. A preparation method of Lamivudine is also disclosed.

11 Claims, 2 Drawing Sheets

LAMIVUDINE OXALATE AND PREPARATION METHOD THEREOF

CROSS-REFERENCE TO RELATED APPLICATIONS

This application is the U.S. National Stage entry of PCT/CN2010/080151, filed Dec. 23, 2010, which claims priority to Chinese Application No. 201010132895.6, filed Feb. 25, 2010, the disclosures of each are herein incorporated by reference.

TECHNICAL FIELD OF THE INVENTION

The present invention relates to a novel salt of Lamivudine and a preparation method thereof. The salt of Lamivudine is cis-Lamivudine oxalate.

BACKGROUND

Nucleotides, analogs and derivatives thereof are a kind of important antiviral therapeutic agents. Numerous nucleotides show good antiviral activities against retrovirus, such as human immunodeficiency virus (HIV), hepatitis B virus (HBV) and human T-cell lymphotropic virus (HTLV).

International patent application PCT/GB91/00706 corresponding to International publication WO91/17159 discloses an antiviral nucleotide-Lamivudine represented by formula I.

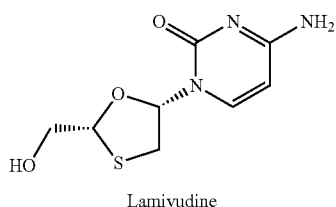

Formula I

Lamivudine 4-amino-1-(2R-hydroxymethyl-[1,3]oxathiolan-5S-yl)-1H-pyrimidin-2-one Most of nucleotides and derivatives thereof contain at least two chiral centers and are present in the form of optical isomers. However, only cis-isomers of such kind of compounds generally exhibit higher biological activity. Therefore, a general stereoselective synthesis of nucleotides that is suitable for industrial production always is a research topic.

WO92/20699 discloses a diastereoselective process for producing optically active cis-nucleotide analogs and derivatives, mainly Lamivudine. The process relies on the use of a particular lewis acid. However, such lewis acid is a highly reactive and unstable compound, which is expensive and has obvious toxicity.

The preparation process as provided in WO92/20699 is optimized in WO/1995/029174, in which a suitable leaving group is selected and oxathiolane having a substituent and leaving group is reacted with pyrimidine so as to avoid the addition of the lewis acid. In addition, WO/1995/029174 further discloses Lamivudine salicylate as an intermediate salt for refining Lamivudine.

The inventors of the present application develop a novel preparation method in which a compound having a chiral center is directly used as a starting material to prepare Lamivudine. The preparation method can ensure to obtain highly stereoselective cis-Lamivudine that can be easily purified and separated, and is suitable for industrial application.

The inventors of the present application conduct a research on the technology as disclosed in WO/1995/029174, especially further evaluate Lamivudine salicylate, and find that this salt still has various defects.

1. Lamivudine salicylate has poor crystallizability and is viscous. A person skilled in the art can understand that a viscous substance easily carries impurities and is difficultly purified. A multi-step refining is needed to obtain Lamivudine with high purity upon using Lamivudine salicylate as an intermediate. Therefore, the industrial cost is higher, and the multi-step refining prolongs the production time and decreases the production efficiency.

2. A substantive amount of triethylamine is added to remove salicylic acid in WO/1995/029174. However, triethylamine has irritation and toxicity to a human body, and needs to be strictly controlled in the quality control of Lamivudine. There exists a need for establishing a related quality control standard to ensure the residual amount of triethylamine meets the quality standard. In addition, a substantive amount of triethylamine is disadvantageous to control the production cost in industrial production.

In order to obtain Lamivudine with high stereoselectivity and high purity but also save on cost, facilitate industrial production and decrease the toxicity of product, the inventors of the present application develop the novel preparation method of the present invention.

SUMMARY OF THE INVENTION

One object of the present invention is to provide Lamivudine oxalate. Lamivudine oxalate has the following structural formula:

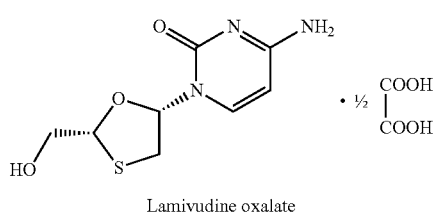

Formula II

Lamivudine oxalate $C_9H_{12}N_3O_5S$
Mol. Wt.: 274.27 wherein the compound as represented by formula II is cis-Lamivudine, i.e. the salt formed by Lamivudine L-isomer and oxalic acid.

Another object of the invention is to provide a preparation method of Lamivudine oxalate.

One preparation method comprises reacting Lamivudine with oxalic acid in a suitable solvent, wherein the suitable solvent comprises water, a polar solvent, such as ethers, tetrahydrofuran, dioxane, or alcohols, such as methanol or ethanol, or mixtures thereof.

Another preparation method comprises the steps of

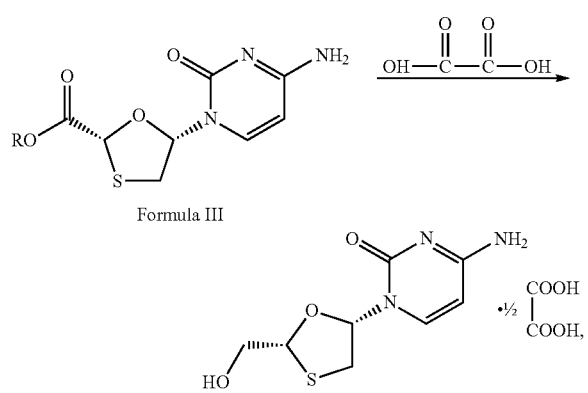

Formula III wherein R is an optionally substituted straight, branched or cyclic alkyl including $C_{1-10}$ alkyl, and the substituents are selected from the group consisting of alkyl, halogen, hydroxy, phenyl and the like. Preferably, R is a chiral group which is beneficial to the isolation of enantiomers, such as menthanyl, phenyl-substituted menthanyl, more preferably L-menthanyl and L-8-phenylmenthanyl. The above-mentioned oxalic acid comprises derivatives of oxalic acid. The compound of formula III is reacted with oxalic acid or the derivatives thereof, then reduced and formed into the salt, wherein the reductant comprises sodium borohydride or potassium borohydride.

One illustrative example is as follows:

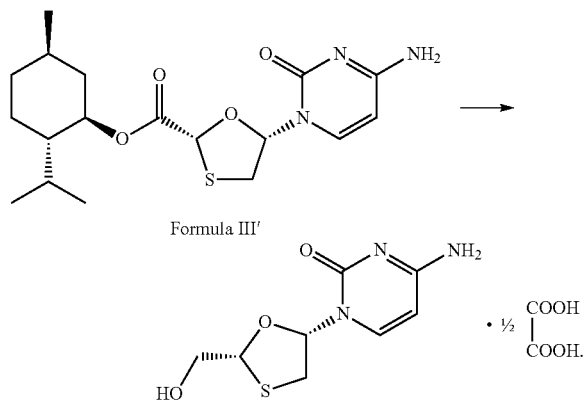

Formula III'

The method for synthesizing Lamivudine oxalate by using the compound of formula III as a starting material comprises: reacting the compound of formula III with sodium borohydride or potassium borohydride in a buffer solution, removing impurities or unreacted starting materials, then reacting the residue with oxalic acid or derivatives thereof to obtain Lamivudine oxalate.

The specific reaction steps are as follows:

(1) preparing a buffer solution, adding a proper amount of ethanol thereto and stirring uniformly, adding the compound of formula III as a starting material to the resultant solution;

(2) adding sodium borohydride solution or potassium borohydride solution dropwise to the solution obtained in step (1), monitoring until the reaction is completed;

(3) treating the solution obtained in step (2) with a solvent or water to remove impurities or unreacted starting materials;

(4) adding oxalic acid or derivatives thereof to the product of step (3), reacting, purifying to obtain Lamivudine oxalate crystal.

More specifically, the preparation method comprises:

(1) preparing a buffer solution, adding a proper amount of ethanol thereto and stirring uniformly, adding CME as a starting material to the resultant solution;

(2) adding sodium borohydride solution dropwise to the solution obtained in step (1) for 1 hr, monitoring until the reaction is completed;

(3) standing the solution obtained in step (2) to separate into two layers, washing the lower water layer with a proper amount of ethanol, combing all of organic solvent layers, and then adjusting pH to 6~6.5 with an acid while maintaining the temperature at 28~32° C., adjusting pH again to 8.0~8.3 with a base, removing ethanol, cooling to room temperature, adding a proper amount of water to dissolve, washing with an organic solvent, combining organic solvent layers, then extracting with water, combining all of water layers, then adding active carbon to discolor, stirring, filtering, and washing the filter cake with water;

(4) adding oxalic acid after combining all of water layers, stirring, centrifuging, washing the filter cake with a small amount of water and then methanol, and drying the product under vacuum at the temperature of 40~45° C. to obtain Lamivudine oxalate crystal.

The buffer solution in step 1 is necessary for the use of the reductant, sodium borohydride or potassium borohydride. For example, the suitable buffer solution is phosphate buffer or borate buffer, such as an aqueous solution of dipotassium hydrogen phosphate, in which the concentration of dipotassium hydrogen phosphate is 20-50%, preferably 25-45%, most preferably 31%. A suitable temperature in step 1 is in the range of from 18° C. to 20° C.

The proper amount of ethanol in step 1 is 4-7 times, preferably 5-6 times of the amount of the starting material.

The concentration of sodium borohydride (or potassium borohydride) solution in step 2 is 5 mol/L, which is preferably prepared as follows: firstly formulating 0.4% of an aqueous solution of sodium hydroxide (or potassium hydroxide), then dissolving an amount of sodium borohydride (or potassium borohydride) in the sodium hydroxide (or potassium hydroxide) solution to prepare 5 mol/L of sodium borohydride (or potassium borohydride) solution.

The expression "monitoring until the reaction is completed" in step 2 means that the amount of the compound of formula III or III' the starting material after reaction is less than 0.5% of the addition amount.

The acid for adjusting pH in step 3 can be hydrochloric acid, sulphuric acid, phosphoric acid, nitric acid and the like, preferably hydrochloric acid, such as 6 mol/L of hydrochloric acid. The base for adjusting pH can be sodium hydroxide, potassium hydroxide and the like.

Lamivudine oxalate of the present invention refers to the salt formed by cis-Lamivudine (Lamivudine L-isomer) and oxalic acid.

The chemical name of the compound of formula III' as the starting material used in the present invention, i.e. CME, is (2R,5S)-5-(4-amino-2-oxo-pyrimidin-1yl)-[1,3]oxathiolan-2-carboxylic acid, 2S-isopropyl-5R-methyl-1R-cyclohexyl ester. The above compound of formula III and CME as the starting materials are commercially available, or prepared according to the method as disclosed in WO/1995/029174.

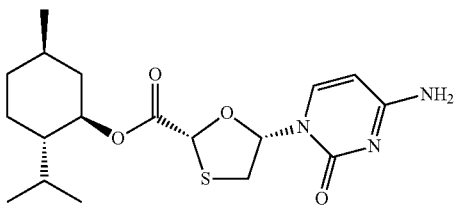

Formular: CME

Another aspect of the present invention provides a method for preparing Lamivudine by using Lamivudine oxalate as a starting material.

We find that Lamivudine oxalate can be easily isolated from a polar solvent and therefore can be converted into Lamivudine in the form of a free base through a conventional method. The conventional method comprises the use of a suitable base, which can be tertiary amine, such as triethylamine.

Specifically, Lamivudine oxalate is added to ethanol, and an amount of triethylamine is added thereto at the temperature of 40~45° C. for 0.5 hr, and stirred for 4 h at the same temperature. The mixture is centrifuged at room temperature, and a product is dried under vacuum at the temperature of 40~45° C. to obtain Lamivudine crystal.

The present invention also provides a method for preparing Lamivudine by using the compound of formula III as a starting material, which comprises reacting the compound of formula III with sodium borohydride or potassium borohydride, then reacting a product with oxalic acid or derivatives thereof to obtain Lamivudine oxalate, and reacting Lamivudine oxalate with a base to obtain Lamivudine,

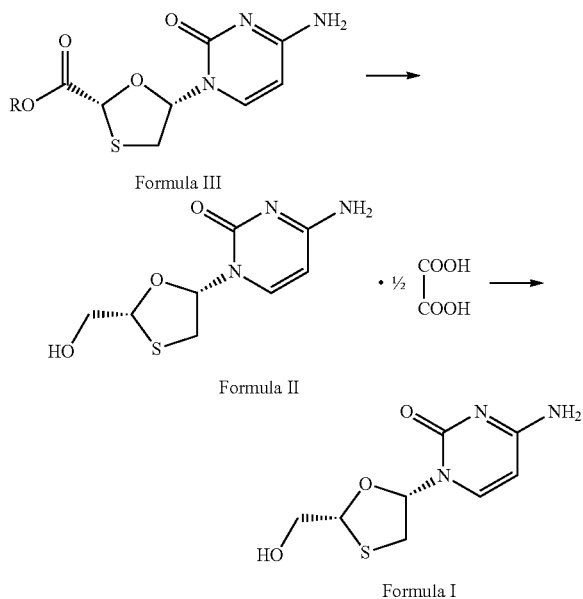

wherein:

R is an optionally substituted straight, branched or cyclic alkyl including $C_{1-10}$ alkyl, and the substituents are selected from the group consisting of alkyl, halogen, hydroxy, phenyl and the like. Preferably, R is menthanyl, phenyl-substituted menthanyl, further preferably L-menthanyl and L-8-phenyl-menthanyl.

Specifically, the compound of formula III is reduced and formed into the salt with oxalic acid or the derivatives thereof, and the corresponding base is freed to obtain the compound of formula I, in which a reagent used in the step of converting the compound of formula III to the compound of formula II comprises sodium borohydride or potassium borohydride.

The present invention provides a crystalline Lamivudine oxalate, and provides a Lamivudine oxalate crystal.

Crystalline Lamivudine oxalate was characterized by X-ray powder diffraction spectrum peak using Cu—Kα radiation, expressed in degree 2θ typically at 21.04, 22.44, 23.46, 23.78, and 25.26, further at 13.94, 14.86, 21.04, 21.30, 22.44, 23.46, 23.78, 25.26, and 33.36, and further at 13.94, 14.86, 16.88, 17.66, 20.34, 21.04, 21.30, 22.44, 23.46, 23.78, 25.26, 28.30, and 33.36. Further, typical crystalline Lamivudine oxalate was characterized by XRD spectrum peak expressed in degree 2θ at 13.94, 14.86, 16.88, 17.66, 18.74, 19.12, 19.66, 20.34, 21.04, 21.30, 22.44, 22.96, 23.46, 23.78, 25.26, 26.78, 28.30, 28.68, 28.96, 30.08, 30.40, 31.92, 32.24, 32.84, 33.36, 34.64, 35.00, and 35.80.

FIG. 1 shows an X-ray powder diffraction spectrum of Lamivudine oxalate crystal as disclosed in the specific example of the present invention.

The above-mentioned Lamivudine oxalate crystal of the present invention is anhydrous, solvent-free or contains little or undetectable amount of water or solvent. Generally, the crystal of the present invention contains less than about 1% water or solvent, typically less than 0.5% water or solvent. The crystal of the present invention may contain less than 20% non-crystalline form. Generally, Lamivudine oxalate crystal of the present invention contains less than 10%, typically less than 1%, generally less than 0.1% non-crystalline form.

Lamivudine oxalate crystal of the present invention has an endothermic transition peak at about 201.9° C. as measured by DSC, and starts the endothermic transition at about 199° C. The thermogram pattern by DSC of one example is shown in FIG. 2, in which the starting temperature of the endothermic transition temperature is 199.23° C., and melting point is in the range of 201.3-202.7° C.

Lamivudine oxalate is a pharmaceutically acceptable salt, and can be used as an antiviral agent as described in WO9117159 and formulated as a pharmaceutical composition.

Lamivudine oxalate as prepared in the present invention is a highly excellent intermediate for preparing Lamivudine with high purity. By comparison, other organic acid salts of Lamivudine, such as salicylate and the like, are viscous, contain more impurities, and are difficult to be dried, which results in the difficulty in preparing Lamivudine with high purity in a next step. However, Lamivudine oxalate is a superior crystal and will not present the above phenomenons during the preparation. Lamivudine as prepared from Lamivudine oxalate has purity of more than 99.5% without refining, which is very advantageous to refine cis-Lamivudine with high purity in the future.

Lamivudine oxalate as provided in the present invention is the salt formed by one molecule of oxalic acid and two molecules of Lamivudine. Lamivudine oxalate of the present invention allows the amount of triethylamine used for removing oxalic acid to prepare Lamivudine to be significantly reduced as compared with other organic acid salts of Lamivudine. Triethylamine is a toxic and combustible chemical agent, which has strong ammonia odor and is slightly fuming in the air. The vapor or liquid of triethylamine can stimulate human skin and mucous membrane, which is absorbed by human body mainly through inhalation, ingestion, skin and the like. After inadvertently inhaled by human body, triethylamine vapor strongly stimulates respiratory tract and can cause pneumonedema and even death. Contacting with eyes and skin, triethylamine can cause chemical burns. Accordingly, the reduction of triethylamine decreases the industrial production cost, more importantly, decreases the use of the toxic agent, increases the security of the production process and decreases the residual chemical agent contained in the final product.

The inventors focus on the comparison of the amounts of triethylamine used for removing organic acids between Lamivudine oxalate and Lamivudine salicylate in the case of equimolar feed ratio.

1. The method for preparing Lamivudine from Lamivudine oxalate is as follows:

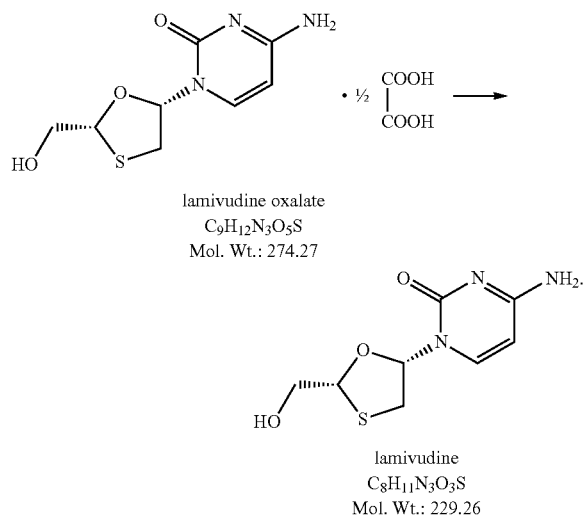

lamivudine oxalate
$C_9H_{12}N_3O_5S$
Mol. Wt.: 274.27 lamivudine
$C_8H_{11}N_3O_3S$
Mol. Wt.: 229.26

To 1000 ml of ethanol was added 120 g of Lamivudine oxalate (prepared by the method of the present invention). 60 ml of triethylamine was added thereto at the temperature of 40~45° C. for 0.5 hour, and stirred at the same temperature for 4 hours. The mixture was centrifuged at room temperature and dried under vacuum at the temperature of 40~45° C. to obtain Lamivudine crystal.

Lamivudine crystal prepared by the above method was measured by liquid phase chromatography. The apparatus and chromatographic conditions are as follows.

Apparatus: WATERS E2695 quaternary pump; detector: WATERS 2489 UV absorption detector; workstation: Empower 2 software; chromatographic column: BDS HYPERSILC18 (250 4.6 mm) by Thermo corporation; mobile phase: methanol-0.025 mol/L ammonium acetate solution (pH is adjusted to pH 3.9 with acetic acid) (5:95); flow rate: 1.0 ml/min; detection wavelength: 277 nm; column temperature: 30° C. The purity of Lamivudine as calculated by normalization method is more than 98%, typically 99.6%.

2. The process for preparing Lamivudine from Lamivudine salicylate is disclosed in part (d) of Example 1 in Chinese patent No. ZL95193466.X.

The Specification of the above patent discloses that 26 ml of triethylamine is needed in the preparation of Lamivudine from 66.7 g of Lamivudine salicylate, which is converted into the molar volume ratio of about 1 mole: 150 ml.

The result by comparison is shown in Table 1.

TABLE 1

The comparison of the used amount of triethylamine between Lamivudine oxalate and Lamivudine salicylate Mole:ml

| Lamivudine oxalate:triethylamine≈ 1:135 | Lamivudine salicylate:triethylamine≈ 1:150 |

It is showed by Table 1 that the used amount of triethylamine is decreased by 15 ml in the preparation of 1 mol Lamivudine from Lamivudine oxalate as the intermediate. This reduced amount of triethylamine will be significant in industrial production. On one hand, such advantage decreases various risks due to the use of the toxic chemical agent, and on the other hand, it decreases the cost of starting materials in industrial production.

EXAMPLES

Figure 1:
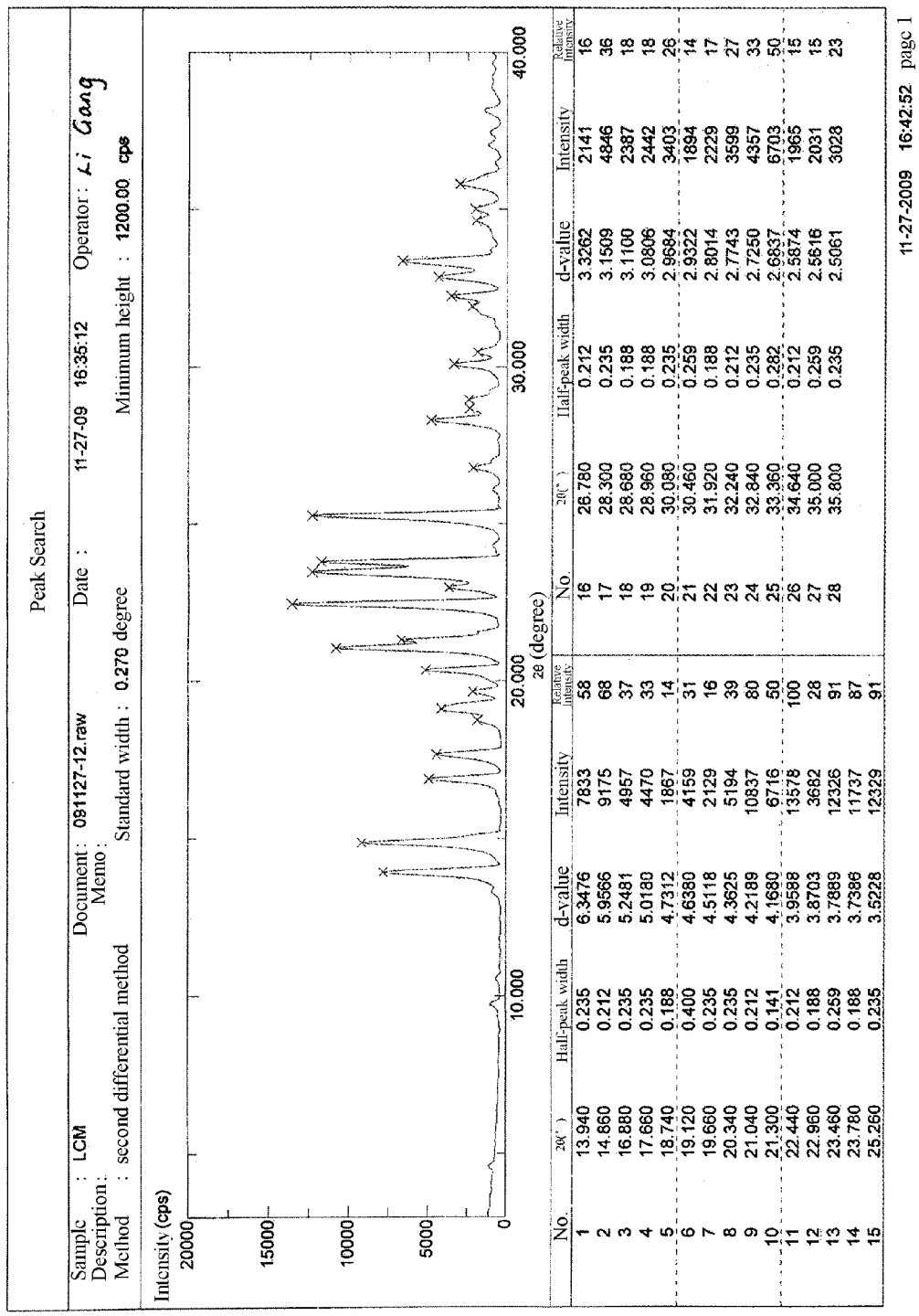
FIG. 1 is X-ray diffraction pattern of Lamivudine oxalate crystal.
Figure 2:
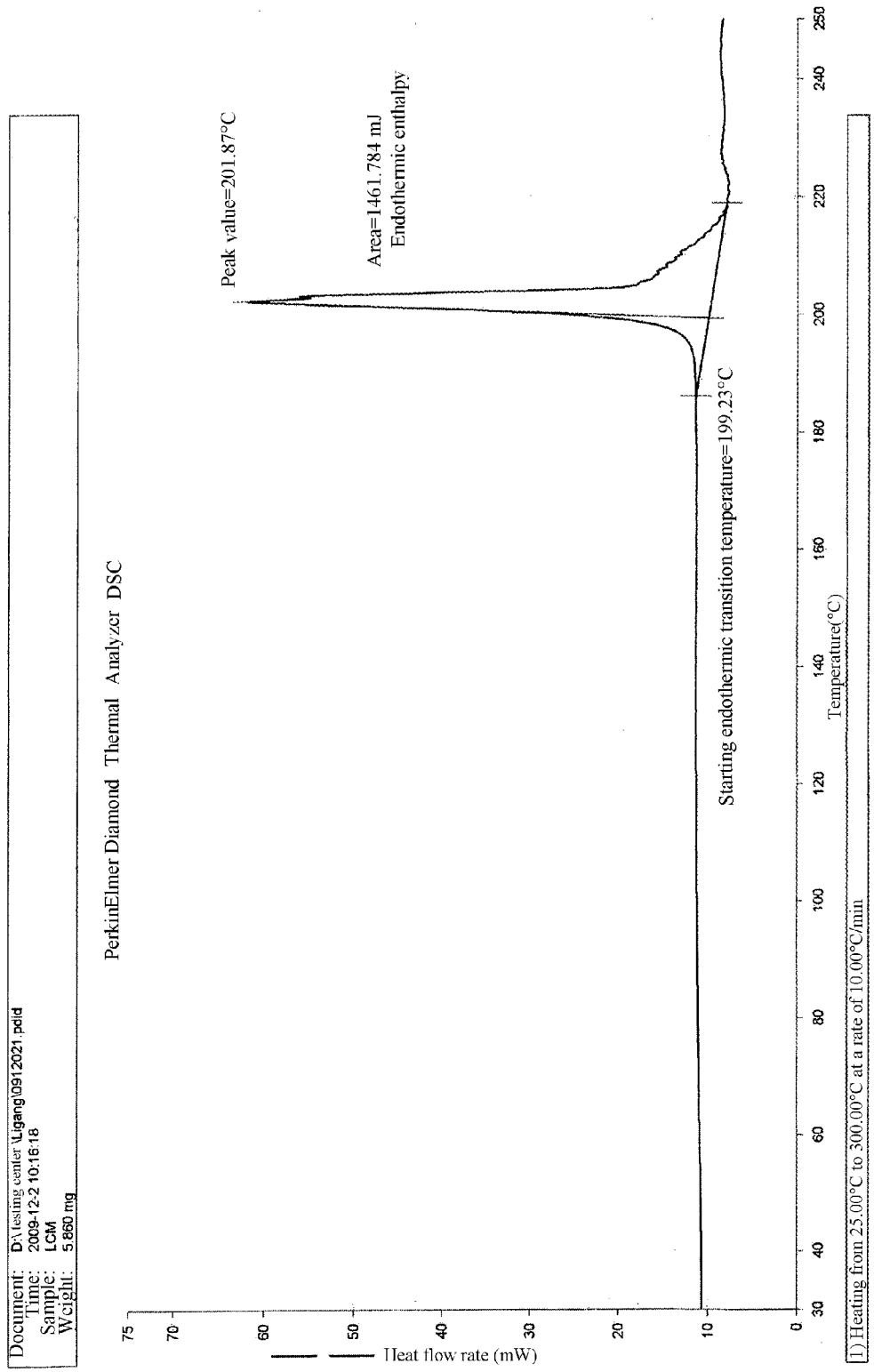
FIG. 2 is differential scanning calorimetry pattern (DSC pattern) of Lamivudine oxalate crystal.

The following examples are intended to further illustrate the present invention and are not intended to limit the scope of this invention.

Example 1

191.8 g of dipotassium hydrogen phosphate was added to 426 ml of water, and the resultant mixture was stirred until complete dissolution while maintaining the temperature at 18° C. To the mixture was added 1 L of ethanol, stirred for 10 minutes, and then 140 g of the starting material for preparing Lamivudine, CME was added at the temperature of 18~20° C. Sodium borohydride solution (which is formulated as follows: firstly formulating 0.4% of an aqueous solution of sodium hydroxide, and then dissolving 28 g of sodium borohydride in 150 ml of the sodium hydroxide solution) was added dropwise to the mixture for 1 hour, and the reaction was monitored until it is completed.

The reaction mixture was standed and separated into two layers, and the lower water layer was washed with 160 ml of ethanol. After combining all organic phases, the pH of the resulting mixture was adjusted with 6 mol/L hydrochloric acid to 6~6.5 at the temperature of 28~32° C. Subsequently, the pH of the mixture was adjusted with an aqueous solution of sodium hydroxide (1.12 kg sodium hydroxide/14 L water) to 8.0~8.3. Ethanol was distilled off, and the residue was cooled to room temperature. To the residue was added 280 ml of water to dissolve and washed with 240 ml of toluene twice. After combining toluene layers, the resulting mixture was extracted with 70 ml of water. After combining all of water layers, 6 g of active carbon was added, and the resulting mixture was stirred at room temperature for 30 minutes. The mixture was filtered, and the filter cake was washed with 180 ml of water. After combining all of water layers, 25 g of oxalic acid was added, stirred, centrifuged, and the filter cake was washed with a small amount of water and then 68 ml of cool methanol. The product was dried under vacuum at the temperature of 40~45° C. to obtain Lamivudine oxalate.

(1) NMR Assay

Apparatus: Bruker AV400 nuclear magnetic resonance spectrometer; solvent: $D_2O$ (heavy water); $^1$HNMR ($D_2O$) $\delta_H$: 3.18 (dd, 1H); 3.49 (dd, 1H); 3.79 (dd, 1H); 3.94 (dd, 1H); 5.25 (t, 1H); 6.03 (d, 1H); 6.24 (dd, 1H); 8.12 (d, 1H).

(2) X-Ray Diffraction Assay

Apparatus: RigakuD/Max-RC X-ray diffractometer; test condition: 40 kv 100 mA; DS=SS=1° RS=0.3 mm; target: Cu; Range: 3.00-40.00; scan Rate: 10.00 Deg/min;

| Peak no. | 2 theta | d-value | I/Io |
|---|---|---|---|
| 1 | 13.94 | 6.3476 | 58 |
| 2 | 14.86 | 5.9566 | 68 |
| 3 | 16.88 | 5.2481 | 37 |
| 4 | 17.66 | 5.0180 | 33 |
| 5 | 18.74 | 4.7312 | 14 |
| 6 | 19.12 | 4.6380 | 31 |
| 7 | 19.66 | 4.5118 | 16 |
| 8 | 20.34 | 4.3625 | 39 |
| 9 | 21.04 | 4.2189 | 80 |
| 10 | 21.30 | 4.1680 | 50 |
| 11 | 22.44 | 3.9588 | 100 |
| 12 | 22.96 | 3.8703 | 28 |
| 13 | 23.46 | 3.7889 | 91 |
| 14 | 23.78 | 3.7386 | 87 |
| 15 | 25.26 | 3.5228 | 91 |
| 16 | 26.78 | 3.3262 | 16 |
| 17 | 28.30 | 3.1509 | 36 |
| 18 | 28.68 | 3.1100 | 18 |
| 19 | 28.96 | 3.0806 | 18 |
| 20 | 30.08 | 2.9684 | 26 |
| 21 | 30.46 | 2.9322 | 14 |
| 22 | 31.92 | 2.8014 | 17 |
| 23 | 32.24 | 2.7743 | 27 |
| 24 | 32.84 | 2.7250 | 33 |
| 25 | 33.36 | 2.6837 | 50 |
| 26 | 34.64 | 2.5874 | 15 |
| 27 | 35.00 | 2.5616 | 15 |
| 28 | 35.80 | 2.5061 | 23 |

(3) For the DSC of Lamivudine oxalate crystal, the starting temperature of the endothermic transition temperature thereof is 199.23° C.; peak value is 201.87° C., and heating rate is 10.00° C./min. Melting point: 201.3-202.7° C. Apparatus: waters 2414.

Example 2

To 1000 ml of ethanol was added 120 g of Lamivudine oxalate (prepared by the method of the present invention). 60 ml of triethylamine was added at the temperature of 40~45° C. for 0.5 hour, stirred at the same temperature for 4 hours, and centrifuged at room temperature. The product was dried under vacuum at the temperature of 40~45° C. to obtain Lamivudine crystal.

To 65 g of the above product was added 1 L of ethanol, heated and refluxed for 30 minutes until the solid was completely dissolved. 4 g of active carbon was added, continued to reflux for additional 30 minutes, and filtered immediately. The reaction mixture was cooled to room temperature for 3-4 hours, stirred at the same temperature for 6 hours, filtered, and the filter cake was washed with a small amount of ethanol. The product was dried under vacuum at the temperature of 40~45° C. to obtain Lamivudine with high purity. The purity was 99.6%.

Melting point of Lamivudine as determined was: 174-177° C.

The invention claimed is:

1. A Lamivudine oxalate, characterized in that the Lamivudine oxalate has the following structural formula:

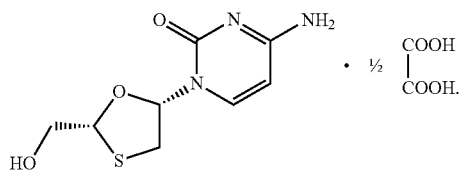 [SMILES: Nc1ccn([C@@H]2CS[C@H](CO)O2)c(=O)n1 ; O=C(O)C(=O)O]

2. The Lamivudine oxalate of claim 1, wherein the Lamivudine oxalate is a crystalline Lamivudine oxalate.

3. The Lamivudine oxalate of claim 2, wherein X-ray powder diffraction peak spectrum of the crystalline Lamivudine oxalate using Cu—Kα radiation is expressed in degree 2θ at 21.04, 22.44, 23.46, 23.78, and 25.26.

4. The Lamivudine oxalate of claim 3, wherein X-ray powder diffraction peak spectrum of the crystalline Lamivudine oxalate is expressed in degree 2θ at 13.94, 14.86, 21.04, 21.30, 22.44, 23.46, 23.78, 25.26, and 33.36.

5. The Lamivudine oxalate of claim 3, wherein endothermic transition peak of the crystalline Lamivudine oxalate measured by DSC is at about 201.9° C. and a starting transition temperature thereof is about 199° C.

6. The crystalline Lamivudine oxalate of claim 4, characterized in that endothermic transition peak measured by DSC is at about 201.9° C. and a starting transition temperature is about 199° C.

7. A method for producing Lamivudine, comprising the steps of:
(a) adding ethanol to the Lamivudine oxalate of claim 1 to produce a first mixture;
(b) adding triethylamine to the first mixture from step (a) to produce a second mixture;
(c) stirring the second mixture;
(d) centrifuging the second mixture; and
(e) vacuum-drying the product from step (d) to produce Lamivudine crystal.

8. The method of claim 7, wherein step (b) is performed at 40-45° C. for 0.5 hour.

9. The method of claim 7, wherein step (c) is performed at 40-45° C. for about 4 hours.

10. The method of claim 7, wherein step (d) is performed at room temperature.

11. The method of claim 7, wherein step (e) is performed at 40-45° C.

* * * * *